(12) United States Patent
Belyaev

(10) Patent No.: US 9,005,935 B2
(45) Date of Patent: Apr. 14, 2015

(54) METHODS AND COMPOSITIONS FOR DNA FRAGMENTATION AND TAGGING BY TRANSPOSASES

(75) Inventor: Alexander S. Belyaev, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/470,087

(22) Filed: May 11, 2012

(65) Prior Publication Data

US 2012/0301925 A1     Nov. 29, 2012

Related U.S. Application Data

(60) Provisional application No. 61/489,073, filed on May 23, 2011.

(51) Int. Cl.

| | |
|---|---|
| C12P 19/34 | (2006.01) |
| C12N 15/10 | (2006.01) |
| C12N 9/12 | (2006.01) |
| C12N 15/00 | (2006.01) |
| C12N 15/87 | (2006.01) |
| C07H 21/02 | (2006.01) |
| C07H 21/04 | (2006.01) |

(52) U.S. Cl.
CPC ........ *C12N 15/1065* (2013.01); *C12N 15/1093* (2013.01)

(58) Field of Classification Search
None
See application file for complete search history.

(56) References Cited

U.S. PATENT DOCUMENTS

| | | | |
|---|---|---|---|
| 5,965,443 A | 10/1999 | Reznikoff et al. | |
| 6,406,896 B1 | 6/2002 | Reznikoff et al. | |
| 7,083,980 B2 * | 8/2006 | Reznikoff et al. | ............ 435/455 |
| 7,608,434 B2 | 10/2009 | Reznikoff et al. | |
| 2010/0120098 A1 * | 5/2010 | Grunenwald et al. | ....... 435/91.2 |

FOREIGN PATENT DOCUMENTS

WO     2010048605 A1     4/2010

OTHER PUBLICATIONS

Heidelberg et al. "DNA sequence of both chromosomes of the cholera pathogen *Vibrio cholerae*," 406 Nature 477-484 (2000).*
Yi et al. "Divalent Cations Stimulate Preferential Recognition of a Viral DNA End by HIV-1 Integrase," 38 Biochemistry 8458-8468 (1999).*
Bassler et al. Vibrio harveyi ATCC BAA-116 chromosome, pp. 1-10 (of 2408) the *Vibrio harveyi* Genome Sequencing Project (2007).*
Lovell et al., "Two-metal active site binding of a Tn5 transposase synaptic complex" 9(4) Nature Structural Biology 278-281 (2002).*
Baker et al., "Identification of residues in the Mu transposase essential for catalysis" 91 Proceedings of the National Academy of Sciences USA 6654-6658 (1994).*
Braam, L.A.M. et al., "A Mechanism for Tn5 Inhibition", J. Biol. Chem., vol. 274(1): pp. 86-92, 1999.
Illumina Genome Analyzer oligonucleotide sequences; Illumina, Inc., 2006 and 2008.
Illumina Genome Analyzer, Genome Analyzer II, and Genome Analyzer IIx oligonucleotide sequences; Illumina, Inc., 2007-2009.
Naumann, T.A. et al., "Tn5 Transposase Active Site Mutants", J. Biol. Chem., vol. 277(20) pp. 17623-17629, 2002.
Nextera DNA Sample Prep Kit User's Manual, Literature # 307, Jun. 2011.
Shendure, J. et al., "Next-generation DNA sequencing", Nature Biotechnology, vol. 26(10), pp. 1135-1145, 2008.
Steininger, M. et al., "Defining characteristics of Tn5 Transposase non-specific DNA binding", Nucleic Acids Research, vol. 34(9), pp. 2820-2832, 2006.
Suganuma, R. et al., "Tn5 Transposase-Mediated Mouse Transgenesis", Biology of Reproduction, vol. 73, pp. 1157-1163, 2005.
Twining, S.S. et al., "Functional Characterization of Arginine 30, Lysine 40, and Arginine 62 in Tn5 Transposase", J. Biol. Chem., vol. 276(25), pp. 23135-23143, 2001.
Weinreich, M.D. et al., "Overexpression of the Tn5 Transposase in *Escherichia coli* Results in Filamentation, Aberrant Nucleoid Segregation, and Cell Death; Analysis of *E. coli* and Transposase Suppressor Mutations", J. Bacteriology, Vo.1 176(17), pp. 5494-5504, 1994.
Syed Fraz et al., "Optimized library preparation method for next-generation sequencing", Nature Methods, vol. 6, No. 10, Oct. 1, 2009.
Caruccio, N., "Preparation of next-generation sequencing libraries using Nextera (TM) technology: simultaneous DNA fragmentation and adaptor tagging by in vitro transposition", Methods in Molecular Biology, vol. 733, Jan. 1, 2011.
Extended European Search Report, European patent application No. 12 168 778.4, date mailed Sep. 27, 2012.
Peterson et al., "Tn5 transposase active site mutations suggest position of donor backbone DNA in synaptic complex," Journal of Biological Chemistry (Jan. 2003): 278(3):1904-1909.
Lovell et al., "Two-metal active site binding of a Tn5 transposase synaptic complex," Nature Structual Biology (Apr. 2002): 9(4):278-281.
Reznikoff, William, "Tn5 as a model for understanding DNA transposition," Molecular Microbiology (Mar. 2003): 47(5):1199-1206.

* cited by examiner

*Primary Examiner* — Celine Qian
*Assistant Examiner* — Nancy J Leith

(57) ABSTRACT

The present invention provides new compositions for transposase-mediated fragmenting and tagging DNA targets. The invention relates to the surprising discovery that use of manganese ions ($Mn^{2+}$) in transposase reactions improves the transposase reaction. It also relates to the surprising discovery that $Mg^{2+}$ ions can be used in a transposase reaction with wild-type and/or engineered transposases at levels much higher than previously thought. The invention provides for the use of naturally-occurring transposases in in vitro reactions, as well as improved schemes for cleaving, tagging, and amplifying target DNA.

22 Claims, 6 Drawing Sheets

Fig. 1
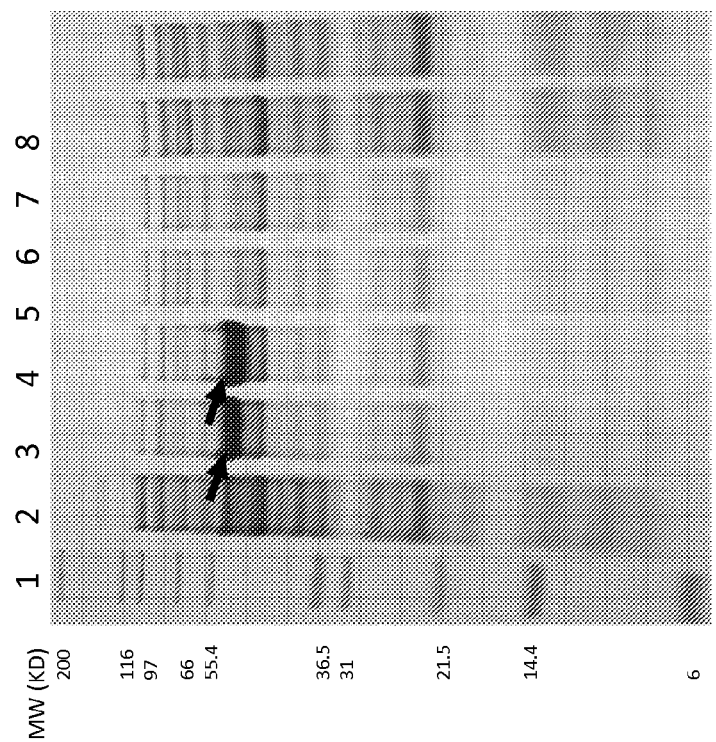
Fig. 1B
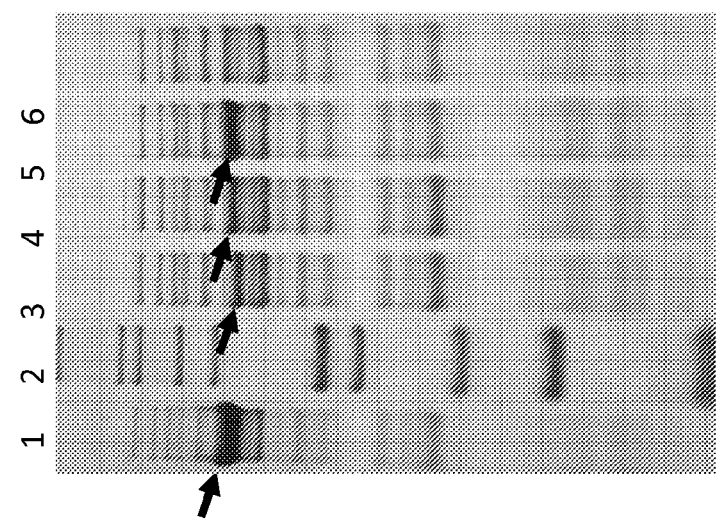
Fig. 1A

Fig. 2
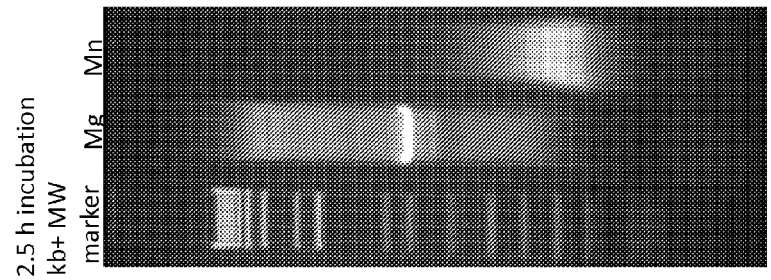
Fig. 2B
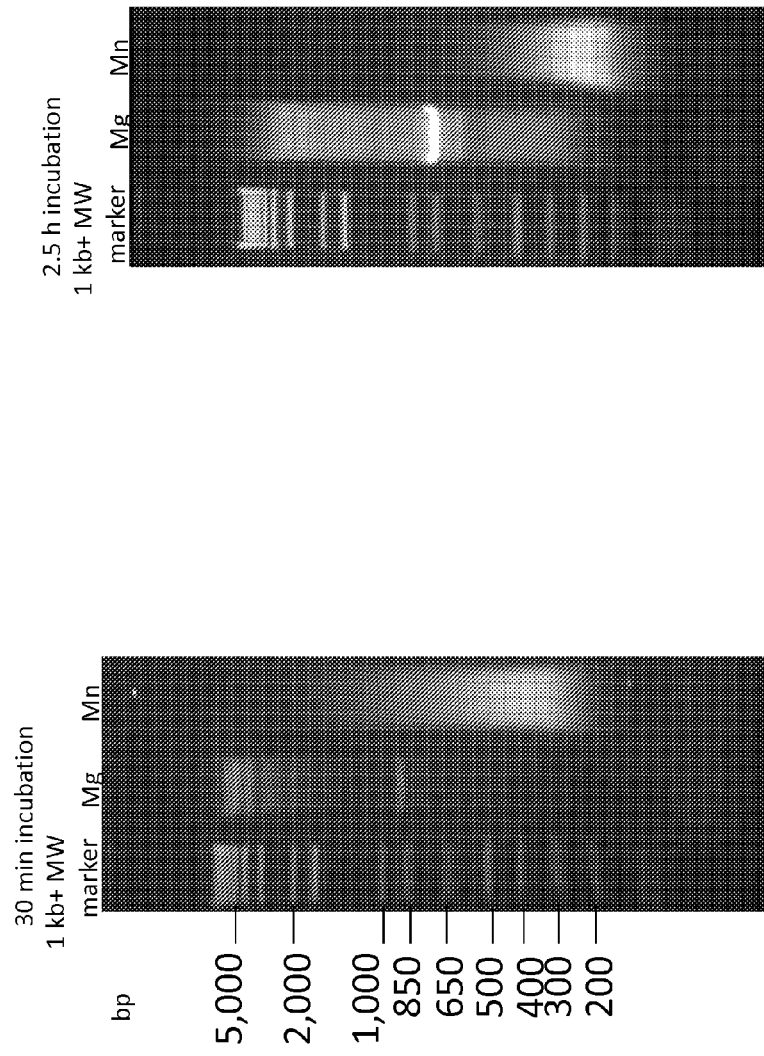
Fig. 2A

Fig. 3A. EPICENTRE design adapted for Vibhar (E)

Fig. 3B De novo Agilent design for Vibhar (A)

METHODS AND COMPOSITIONS FOR DNA FRAGMENTATION AND TAGGING BY TRANSPOSASES

CROSS-REFERENCE TO RELATED APPLICATIONS

This application relies on the disclosure of, and claims the benefit of the filing date of, U.S. provisional patent application No. 61/489,073, filed 23 May 2011, the entire disclosure of which is hereby incorporated herein by reference.

BACKGROUND OF THE INVENTION

1. Field of the Invention

The present invention relates to the field of molecular biology. More specifically, the invention relates to methods and compositions for cleaving DNA molecules using transposases and preparing the cleaved DNA molecules for analysis by tagging the molecules with pre-selected sequences of interest. Among other things, the invention relates to the areas of in vitro amplification of nucleic acids, sequencing of nucleic acids, and screening of DNA libraries for sequences of interest.

2. Description of Related Art

Fragmentation of genomic DNA is a crucial step in DNA sample preparation for high-throughput sequencing. Traditionally used methods, such as DNA fragmentation using DNase I, are very unreliable and often result in DNA fragmentation that is either insufficient or too extensive. In either case, the yield of DNA fragments of useful size (about 200-800 base pairs (bp)) is low. This difficulty has been overcome by controlled DNA fragmentation using oligonucleotide-transposase complexes, such as the NEXTERA™ system from Epicentre. Such complexes are comprised of a dimer of modified Tn5 transposase and a pair of Tn-5 binding double-stranded DNA (dsDNA) oligonucleotides containing a 19 bp transposase-binding sequence, or inverted repeat sequence (IR). In the NEXTERA™ system, an engineered, non-native 19 bp transposase binding sequence is used, which provides more efficient DNA fragmentation than the native Tn5 IR sequence. This binding sequence is referred to as "mosaic".

Unlike DNase, a single molecule of which can generate numerous breaks in a target DNA, the transposase complex is believed to create only one DNA cleavage per complex. Therefore, unlike with DNase I, the degree of DNA fragmentation is easily controlled during transposase fragmentation. Furthermore, specific nucleotide tags combined with the mosaic sequence can be attached in this transposase-mediated DNA fragmentation process, which is useful for DNA amplification in PCR and attaching the DNA fragments to sequencing chips.

Typically Mg(II) ions (also referred to herein as $Mg^{+2}$ or $Mg^{2+}$) are used as a cofactor with enzymes that exhibit DNA fragmentation activity. This is not surprising, as by examining the melting temperature of double-helical DNA in the presence of different metal ions it has been established that the preference for phosphate association was found to decrease in the order $Mg(II)>Co(II)>Ni(II)>Mn(II)>Zn(II)>Cd(II)>Cu(II)$. The reaction of transition-metal complexes with polynucleotides generally fall into two categories: (i) those involving a redox reaction of the metal complex that mediates oxidation of the nucleic acid; and (ii) those involving coordination of the metal center to the sugar-phosphate backbone so as to mediate hydrolysis of the polymer. Though Mg(II) is the strongest binder, it is not necessarily the best cofactor. Enzymatic DNA cleavage can be influenced by many parameters, in particular by DNA conformation contingent upon the nature of the metal ion binding to the DNA. Furthermore, binding of a particular metal ion to the enzyme itself could affect protein conformation, protein-protein interactions, for instance protein dimerization that might influence the activity; and protein-nucleic acid interactions, i.e., modulating the speed of the reaction and the DNA cleavage specificity.

To date, the only transposase that is known to be suitable for DNA fragmentation and tagging is a modified Tn5 transposase. From the onset, Tn5 transposase has been problematic in several respects. First of all, the native transposase was practically impossible to produce, as it is toxic for *E. coli* when expressed from a strong promoter. However, it was possible to overcome this difficulty by deleting several N-terminal amino acids (Weinreich et al., J. Bacterial, 176: 5494-5504, 1994). Though this solved the toxicity problem, and the N-terminally truncated transposase was produced at high yield, it possessed very low activity. Therefore, several other mutations were introduced to increase its activity (U.S. Pat. No. 5,965,443; U.S. Pat. No. 6,406,896 B1; U.S. Pat. No. 7,608,434). However, this did not solve all of the problems. The mutated enzyme is stable only in high salt, such as 0.7M NaCl, (Steiniger et al., Nucl. Acids Res., 34: 2820-2832, 2006), but it quickly loses its activity at the low salt conditions that are required for the transposase reaction, with a half-life only 2.4 min in the reaction mixture. Thus, DNA fragmentation reactions using this transposase are typically performed in 5 minutes, and very large amounts of enzyme are used. Despite the fact that high salt concentration is maintained throughout the purification process, the purified enzyme is largely inactive; thus, 9.4 times excess of enzyme over nucleotides is typically used to form Tn5 transposase-oligonucleotide complexes (Naumann and Reznikoff, J. Bioi. Chem., 277:17623-17629, 2002). In addition, the transposase is prone to proteolytic degradation. Therefore, the degradation-prone sites were mutated. Interestingly, these mutations resulted in drastic reduction of the in vivo activity, but had little effect on the in vitro activity (Twining et al., J. Bioi. Chem., 276: 23135-23143, 2001). Overall, Tn5 transposase is difficult to produce, it is required in large amounts, and it is very expensive.

SUMMARY OF THE INVENTION

The present invention improves on existing technologies for DNA fragmenting and tagging using transposases. In embodiments, the invention provides new reaction conditions, which include manganese ions instead of magnesium ions, for transposase-mediated cleavage of target nucleic acids with concomitant tagging of the resulting DNA fragments. The invention thus broadens transposase reaction conditions to include magnesium ions, manganese ions, or both. Preferably, the reaction conditions also include relatively low alkali metal ion, such as potassium ion, concentrations. The resulting tagged DNA fragments find use in many molecular biology applications, including, but not limited to, next generation sequencing, Polymerase Chain Reaction (PCR) techniques, and gene cloning and genome analysis. Using the reaction conditions disclosed herein, native transposases (i.e., transposases having amino acid sequences not differing from amino acid sequence found in nature; e.g., non-recombinant), as well as modified transposases (i.e., transposases having amino acid sequences differing from the amino acid sequence found in nature; e.g., recombinant) can be used for in vitro DNA fragmentation and tagging at relatively low concentrations and relatively short reaction times. Native transposases can be obtained either from native or recombinant hosts, whereas modified transposases can be obtained only from recombinant hosts. The reaction conditions thus provide an improvement over the current art.

The present invention also improves on existing technologies for preparing DNA substrates for next generation sequencing. The present invention provides a new method for preparing such DNA substrates that incorporates two different transposase recognition sequences per DNA fragment created, coupled with independently tagged primers for amplification of the DNA fragments. The method allows for preparation of tagged products using only two primers.

In a first aspect, the invention provides compositions, preferably aqueous compositions, comprising a transposase and manganese ions (Mn(II)) at a concentration of from about 1 mM to about 100 mM or even higher. It has surprisingly been found that use of Mn(II) ions at these concentrations provides superior transposase-mediated cleavage activity as compared to use of magnesium ions (Mg(II)), which are typically used in Tn5 transposase reactions. However, under conditions used in the present invention magnesium ions can be used, alone or in combination with manganese ions, to provide superior results as compared to prior art disclosures relating to the use of MG(II)-containing reaction compositions. Indeed, the finding is contrary to the prevailing belief in the art that optimal activity for transposases is found in compositions containing $Mg^{+2}$ (see, for example, www dot epibio dot com slash item.asp?id+292, which indicates that Tn5 transposase complexes are inactive in the absence of $Mg^{+2}$, but active in the presence of that ion, but at relatively low levels).

In preferred embodiments, the Mn(II) concentration, the Mg(II) concentration, or the concentration of both, ranges from about 5 mM to about 40 mM, such as from about 10 mM to about 20 mM. Where both ions are present, the concentration of each can range from about 1 mM to about 1000 mM each, such as from about 5 mM to about 40 mM, including about 10 mM to about 20 mM. Data obtained by the inventor show that these concentration ranges are equally suitable for fragmentation of both human DNA and lambda phage DNA. Thus, it appears that the advantageous use of $Mn^{+2}$ ions, $Mg^{+2}$, or both, in a transposase reaction mixture according to the present invention is not limited to cleavage of a particular type of DNA, but is rather widely applicable. Of course, those of skill in the art will immediately recognize that every particular value for $Mn^{+2}$ and $Mg^{+2}$ ion concentration within the disclosed ranges is envisioned by the present invention, without the need for each and every value to be specifically recited. While each value is encompassed as part of the invention, an exhaustive listing of the values is omitted for the sake of brevity. Such a concept is applicable to all ranges of values disclosed herein.

Interestingly, and further surprisingly, it has been found that the relatively wide range of $Mn^{+2}$ and $Mg^{+2}$ concentrations, or combinations of the two, such as from about 1 mM to about 100 mM each or total, reduce the sequence specificity of the transposase. Reduced sequence specificity is an important characteristic for a transposase used to create DNA fragments for next generation sequencing.

In preferred embodiments, the concentration of salts other than $Mn^{+2}$ and $Mg^{+2}$, such as alkali metals salts such as $K^+$ or $Na^+$ glutamate, is relatively low, for example at a concentration of about 50 mM or less. It is widely accepted that salts other than magnesium salts, such as potassium ions ($K^+$), are advantageously included in transposase reaction mixtures. It has been surprisingly found that transposase activity was further improved by limiting the amount of potassium ions in the transposase reaction mixture. This result should be applicable to other non-magnesium salts. This result, too, was unexpected, as the inventor was unaware of any studies reporting improved transposase activity in low potassium ion compositions. The surprising finding improves transposase-mediated cleavage activity as compared to the higher potassium ion concentrations typically used in Tn5 reactions, which is 75 mM to 100 mM. In exemplary embodiments, the non-magnesium or non-manganese salt (e.g., potassium ion) concentration in the composition is about 40 mM or less, such as about 35 mM or less. Preferably, the ion concentration is about 25 mM; however, it could be less than that in certain embodiments, such as 25 mM to 1 mM or less than 1 mM. As with the disclosure of other concentrations or ranges herein, the skilled artisan should recognize that the invention encompasses every particular value for these ion concentrations within the stated ranges.

The transposase for the compositions (and methods) of the invention can be any protein having transposase activity. It can be a naturally occurring transposase or a recombinant transposase. Preferably, the transposase is isolated or purified from its natural environment (i.e., cell nucleus or cytosol), at least to some extent. For recombinantly produced transposases, preferably the recombinant transposase is isolated or purified from the recombinant host environment (i.e., cell nucleus or cytosol), at least to some extent. Most preferably, the transposase is purified away from other cellular components to a level of 90% or greater prior to inclusion in compositions of the present invention. Preferably, the transposase is at a level of about 95% or greater, such as about 98% pure, about 99% pure, or greater than 99% pure. Purity is determined based on common techniques for determining purity, such as by or Coomassie blue staining of protein gels, silver staining of protein gels, HPLC, or other sensitive techniques for detecting proteins in samples. The ability to use a naturally occurring transposase is a distinct advantage over other systems available in the art, as this is the first disclosure of reaction conditions under which a naturally occurring transposase is active in vitro at a level suitable for commercial DNA fragmenting and tagging. In exemplary embodiments, the transposase is a member of the IS4 family of transposases, such as one that is naturally found in *Vibrio* species, including, but not limited to, *Vibrio harveyi*.

An exemplary embodiment of the invention relates to the *Vibrio harveyi* transposase. This enzyme was discovered through a search of publicly available databases. It was previously identified in the art based on computer translation of the underlying nucleic acid as an open reading frame that encoded a hypothetical protein of unknown function. The present inventor subsequently expressed the protein from the DNA, purified the protein, and identified it as a transposase. To the inventor's knowledge, this is the first disclosure of expression, purification, and determination of the enzymatic activity of the hypothetical protein. The naturally occurring enzyme sequence is available under NCBI/GenBank Accession No. YP_001446289, and has the sequence as indicated in Appendix A. As used herein, this enzyme is referred to at times as "Vibhar". The invention thus relates in embodiments to the novel use of Vibhar as a transposase.

While the naturally occurring Vibhar transposase is exemplified herein, it is to be understood that other naturally occurring transposases are included within the scope of this invention. Furthermore, engineered transposases, which are derived from naturally occurring transposases but include one or more amino acid deletions, substitutions, or additions, are also encompassed. It is to be understood that the modifications made to the naturally occurring transposases do not abolish the transposase activity of the enzyme, although the modifications may alter the specificity or activity in some way. Those of skill in the art can recognize residues that are important in function of the various transposases encompassed by the invention with reference to conserved residues among transposases based on alignment of sequences of transposases. Preferably, the engineered transposases share at least 50% sequence identity with a naturally occurring transposase, preferably the transposase from which the engineered enzyme is derived. Other preferred levels of identity include at least 60%, at least 70%, at least 80%, at least 90%, at least 95%, at least 98%, and at least 99%. Again, those of skill in the art will immediate recognize that all specific values for percent identity falling within these ranges are contemplated by the invention, without the need for Applicant to specifically list all of the values herein.

For example, residues D93, D193, and E327 (amino acid numbering based on the amino acid sequence of GenBank Accession No. YP_001446289.1) are active site residues. Those of skill in the art would immediately recognize that those residues should be maintained if the purpose of making a recombinant protein is to retain enzymatic activity, but would target those residues if a non-active enzyme was desired, or if an enzyme with altered activity were desired (e.g., by making conservative changes or changes that conserved the three-dimensional presentation in one or more of these residues). Further, one of skill in the art would recognize that the following residues should be avoided as sites of mutation if little or no change in activity for the recombinant enzyme were desired, but would be targeted if altered activity were desired: W9, L19, D21, R23, R28, L29, A56, Y57, R58, N62, I70, T78, T94, L108, G109, H124, L127, G137, Q141, R146, K165, E166, W170, R194, E195, D197, R206, R215, L229, R255, L299, L301, L302, P306, A313, Y320, R323, W324, H330, K334, G337, E341, R353, A362, R364, L386, L394, A413, L420, G422, K427, W438, and G440. Additionally, one of skill in the art would understand the importance of the conserved "YREK" (SEQ ID NO:1) motif (residues 320-334 of GenBank Accession No. YP_001446289.1), which is involved in the enzymatic activity of the IS4 family of transposases; the importance of the conserved "DDT" motif (residues 88-99 of GenBank Accession No. YP_001446289.1), which is involved in catalysis and contact of the transposase with target DNA phosphate backbone in the IS4 family of transposases; and the importance of the conserved "DREAD" (SEQ ID NO:2) motif (residues 193-197 of GenBank Accession No. YP_001446289.1), which is involved in target and/or donor DNA binding. Yet again, those of skill in the art would understand the importance of residue W299, which is involved in the hairpin cleavage mechanism of the enzyme. Other residues of interest for structure-function considerations in making recombinant transposases are the various residues identified by Reznikoff et al. (Reznikoff, W. S. et al., "Comparative Sequence Analysis of IS50/TN5 Transposase", Journal of Bacteriology, Vol. 186, No. 24, December 2004, p. 8240-8247), incorporated herein by reference in its entirety.

The compositions of this aspect of the invention can be created for any number of purposes, and are not limited to those specifically discussed herein. Exemplary compositions are those useful for storing transposases (with or without nucleic acids comprising the transposases' recognition sequences), for cleaving or fragmenting target DNA, and for cleaving and tagging target DNA. As such, the compositions can comprise DNA molecules that contain recognition sequences for transposases. The DNA molecules in a particular composition can comprise a single recognition sequence for a particular transposase. Different ds or ss DNA sequences (tags) are attached to a transposase recognition sequence to allow PCR amplification, attachment of generated DNA fragments to sequencing chips, such as Illumina chips (as known in the art), and allow identification of the source of the target DNA library, such as Index sequences. For the purpose of applicability to next generation sequencing, it is preferred that about a half of the DNA fragment ends are tagged with one type of tag and another half with a different tag, whereas one kind of tag is attached to one end of the target DNA fragment, and another type to the opposite end to allow reading of a DNA fragment in both directions. Further improvement is achieved by combining two different transposase recognition sequences, i.e., that some (e.g., about 50%) of the DNA molecules in a particular composition comprise a first recognition sequence for a transposase and the remaining DNA molecules comprise a second, different recognition sequence. The recognition sequence can be a naturally occurring sequence for the transposase, or can be an engineered sequence that provides additional or alternative functions for the DNA molecule.

In exemplary embodiments, the recognition sequence is the same sequence for each end of the target DNA to be fragmented. In some embodiments, the two sequences are identical or substantially identical, having at least 90% (i.e., 90%-100%) sequence identity with each other. In some other embodiments, the two sequences are different, having less than 90% (i.e., 89% or less, a minimum being about 30%) identity with each other. However, it is preferred that both recognition sequences are recognizable by the transposase being used in conjunction with them. In exemplary embodiments, the recognition sequence is one for *V. harveyi*, and comprises the sequence: 5'-ctgtctcttgatcacaagt-3' (SEQ ID NO:3); 5'-acttgtgatcaagagacag-3' (SEQ ID NO:4); 5'-agatgt-gatcaagagacag-3' (SEQ ID NO:5); or 5'-ctgtctcttgatcacatct-3' (SEQ ID NO:6). In some embodiments, the first recognition sequence, the second recognition sequence, or both, is a double stranded DNA sequence comprising a sequence for one strand of SEQ ID NO:4, SEQ ID NO:5, and/or SEQ ID NO:6. In some embodiments, the first recognition comprises a sequence for one strand of SEQ ID NO:4, and the second recognition sequence is a modified recognition sequence for a transposase from *Vibrio harveyi* that comprises a sequence for one strand of SEQ ID NO:5.

Any number of additional substances can be included in the compositions of this aspect of the invention. The identity, number, and amount of the various additional components will typically be dictated by the application for the composition or the specific requirements for a particular transposase for optimal activity.

In some embodiments, compositions comprise cleaved or fragmented target DNA to which adaptors have been covalently bonded. Such DNA molecules result from the action of the transposase, which chemically bonds the DNA molecules containing the transposase recognition sequence(s) to the target DNA, resulting in cleavage of the original target DNA and formation of DNA fragments having the transposase recognition sequences at their ends.

In certain embodiments, the adaptor/target DNA molecules further comprise one or more primers hybridized to one or both strands and/or to single stranded adaptor/target DNA molecules to which a primer is hybridized. The primers are suitable for use as amplification or sequencing primer. In preferred embodiments, the primers used for PCR amplification include 3' sequence regions that include sequences that are part of the transposase recognition sequence(s). Preferably, these primers include 5' sequences that do not include sequences that are part of the transposase recognition sequence(s). Further, it is preferable that one or both (preferably both) include sequences that allow for the nucleic acid amplified from the primer(s) to comprise a sequence that allows the amplified product to hybridize to a solid support for sequencing. As used herein, such sequences are referred to at times as "tag" sequences for attachment to specific oligonucleotides on the chip. Preferably, two PCR amplification primers are used that have sequences in their 5' regions that differ between the two primers; these sequences can act as adaptor sequences. In such embodiments, high specificity can be achieved for amplification or sequencing of the target DNA. Preferably, the primers include a sequence that is suitable for use as a detectable signal, such as a tag for an "Illumina" detection scheme. In highly preferred embodiments, the tag for one strand is different than the tag for the other strand, resulting in tagged nucleic acids having unique tag signatures.

In exemplary embodiments, the primer comprises the sequence: 5'-aatgatacggcgaccaccgagatctacacgctgacgtcgagacttgtga-3' (SEQ ID NO:7); or 5'-caagcagaagacggcatacgagatcggtggagctgtgcgtagatgtga-3' (SEQ ID NO:8).

The invention also provides nucleic acids encoding the transposases of the invention. In general, this aspect of the invention relates to all nucleic acids, naturally occurring or engineered/recombinant, that encode a protein with transposase activity, and that shows activity in compositions according to the invention. Exemplary nucleic acids according to this aspect of the invention include those showing at least about 50% sequence identity with the naturally occurring nucleic acid that encodes the *V. harveyi* transposase, the sequence for which is publicly available, as discussed above. Preferably, the nucleic acid shows at least about 60% sequence identity, at least about 70% sequence identity, at least about 80% sequence identity, at least 90% sequence identity, at least 95% sequence identity, at least about 96% sequence identity, at least about 97% sequence identity, at least about 98% sequence identity, or at least about 99% sequence identity. As with other ranges recited in this document, those of skill will immediately understand that the invention contemplates each and every value encompassed by the ranges specifically recited in this paragraph, without the need for Applicant to specifically recite each value separately. Preferably, the nucleic acid is isolated or purified from one or more other cellular components prior to its use in preparing a transposase of the invention.

In one aspect of the invention, kits are provided. In general, kits according to the invention contain some or all of the components of compositions of the invention, or comprise some or all of the substances necessary for practice of a method of the invention. As understood in the art, the components can be packaged together to provide a single, shippable and/or storable unit for delivery and/or organization of the components.

In another aspect, methods of transposase-mediated fragmenting and tagging of a target DNA are provided. In one embodiment, the method comprises: (A) combining 1) a first DNA molecule comprising at least a portion that is double stranded, wherein the double stranded portion comprises a recognition sequence for a transposase and the DNA molecule further comprises a portion that does not comprise a recognition sequence for the transposase; 2) a second DNA molecule comprising at least a portion that is double stranded, wherein the double stranded portion comprises a recognition sequence for the transposase and the DNA molecule further comprises a portion that does not comprise a recognition sequence for the transposase, wherein the non-recognition portion of the sequence is different from the non-recognition portion sequence of the first DNA molecule; and 3) the transposase, wherein combining the three substances allows them to interact; and (B) combining the interacted substances with a target DNA molecule and $Mn^{+2}$ ions, $Mg^{+2}$ ions, or both, under conditions whereby the interacted substances associate with the target DNA and cleave the target DNA molecule via transposase-mediated cleavage to provide a cleaved DNA product.

In yet another embodiment, the method comprises: (A) combining 1) the target DNA molecule; 2) a first DNA molecule comprising at least a portion that is double stranded, wherein the double stranded portion comprises a first recognition sequence for a transposase; 3) a second DNA molecule comprising at least a portion that is double stranded, wherein the double stranded portion comprises a second recognition sequence for the transposase; and 4) the transposase; and (B) subjecting the combination to conditions whereby the first DNA molecule, second DNA molecule, and transposase can associate with the target DNA molecule and cleave the target DNA molecule via transposase-mediated cleavage to provide a cleaved DNA product, wherein the conditions include 1-100 mM $Mn^{+2}$, 1-100 mM $Mg^{+2}$, or 1-100 mM of a combination of $Mn^{+2}$ and $Mg^{+2}$ ions.

In certain embodiments, the second DNA molecule comprises at least a portion that is double-stranded and differs from the first DNA sequence both in the transposase recognition portion and the non-transposase recognition portion. As such, the invention encompasses embodiments in which the first recognition sequence is different from the second recognition sequence. While in some embodiments, the components to be combined are combined all together at the same time, in preferred embodiments, the first DNA molecule, the second DNA molecule, and the transposase are combined to make a complex prior to combining the complex with the target DNA molecule.

The method can be practiced with any naturally occurring (i.e., wild-type) transposase or with an engineered transposase. The use of a wild-type transposase within the context of the present invention provides an advantage over prior art disclosures. Further, and independently, in embodiments, the reaction conditions for the present invention provide superior results as compared to prior art methods. In exemplary embodiments, the transposase is an IS4 family transposase, such as one naturally found in *Vibrio* species, including, but not limited to *Vibrio harveyi*. As such, the recognition sequence for the transposase can be a naturally occurring sequence. It may also be a sequence that is engineered to have properties other than those exhibited by the naturally occurring sequence, such as stronger (or weaker) binding for the naturally occurring transposase or for an engineered transposase.

In embodiments, the first recognition sequence, the second recognition sequence, or both, is a recognition sequence for a transposase from *Vibrio harveyi*. For example, the first recognition sequence, the second recognition sequence, or both, can be a double stranded DNA sequence comprising a sequence for one strand of: 5'-acttgtgatcaagagacag-3' (SEQ ID NO:4). Alternatively or additionally, the first recognition can comprise a sequence for one strand of: 5'-acttgtgatcaagagacag-3' (SEQ ID NO:4), and the second recognition sequence can be a modified recognition sequence for a transposase from *Vibrio harveyi* that comprises a sequence for one strand of: 5'-agatgtgatcaagagacag-3' (SEQ ID NO:5). Alternatively or additionally, the first recognition, the second recognition sequence, or both, can be a double stranded DNA sequence comprising a sequence for one strand of: 5'-agatgtgatcaagagacag-3' (SEQ ID NO:5). In embodiments, the first recognition sequence, the second recognition sequence, or both, is a modified recognition sequence for a transposase from *Vibrio harveyi* that differs from the naturally occurring recognition sequence by at least one nucleotide, but preferably fewer than 10 nucleotides.

In some embodiments of the invention, $Mn^{+2}$ ions and/or $Mg^{+2}$ ions are used to improve the fragmentation/cleavage and/or tagging of target DNA by transposases. In those embodiments, the $Mn^{+2}$ and/or $Mg^{+2}$ ions concentration in the cleavage and/or tagging conditions is between about 1 mM and about 100 mM, such as from between about 5 mM and about 40 mM, or from between about 10 mM and about 20 mM, either individually or in combination. In some embodiments, non-$Mn^{+2}$ and/or non-$Mg^{+2}$ ions salts, such as alkali metal salts, are present at a relatively low concentration, such as below 50 mM, such as about 25 mM or lower. Where potassium salts are present, they are preferably present at a concentration of about 25 mM.

The method of the invention can further comprise adding adaptors to the fragmented and tagged DNA targets. As such, the invention further relates to another aspect, which is a method of adapting the tagged transposase-fragmented DNA molecules for subsequent analysis. Methods for adding adaptors to fragmented and tagged DNA targets are known in the art, and any of the available techniques can be used according to the invention to arrive at a DNA suitable for use in subsequent analyses, such as next generation sequencing, microarray analysis, etc. The DNA can be submitted for such analysis either directly after reacting with transposase, or after PCR amplification, contingent upon the amount of the starting material and the requirements of the analysis.

In embodiments, the adaptors of the invention comprise 1) a 3' region that can hybridize to at least a portion of the fragmented and tagged DNA target, and 2) a 5' region that does not hybridize to the fragmented and tagged DNA target. The 3' region preferably includes a nucleotide sequence that hybridizes to one strand of the fragmented and tagged target DNA under conditions suitable for in vitro amplification, such as PCR. In highly preferred embodiments, the 3' region comprises a nucleotide sequence that hybridizes to the fragmented and tagged DNA target within the transposase recognition site of the DNA target. On the other hand, the 5' region of the adaptors includes a sequence that does not hybridize to the DNA target under the conditions that allow for hybridization of the 3' region. Rather, the 5' region includes a sequence that allows the amplified product (the adaptors can be considered as primers for amplification of the DNA target) to associate with another nucleic acid, such as one bound to a solid phase support (e.g., a nucleic acid on a chip). Non-limiting examples of such sequences are sequences useful for binding the DNA target to an Illumina substrate or a Roche 454 substrate.

In embodiments, two adaptors are bound to the fragmented and tagged DNA target. Preferably, the 5' region of each of the adaptors comprises a nucleotide sequence that is different from the other adaptor. However, it is preferred that both 5' sequences are suitable for use in the same format for analysis (e.g., both include a sequence that can be attached to Illumina chips, Roche chips, etc).

Of course, the adaptors can include "bar codes", as are known in the art.

BRIEF DESCRIPTION OF THE DRAWINGS

The accompanying drawings, which are incorporated in and constitute a part of this specification, illustrate embodiments of the invention, and together with the written description, serve to explain certain principles and features of the invention.

FIG. 1A and FIG. 1B show SDS-PAGE gel results of crude extracts of *E. coli* cells expressing various transposases. Protein bands corresponding to transposases are indicated by arrows. FIG. 1A: Cultivation at 37° C. Lane 1—hypothetical protein VIBHAR_03113, *Vibrio harveyi* ATCC BAA-1116, YP_001446289; Lane 2—Mark12 molecular weight marker (Invitrogen); Lane 3—transposase from *Photobacterium profundum* SS9, YP_133439; Lane 4—transposase from *Vibrionales* bacterium SWAT-3, ZP_01815141.1; Lane 5—conserved hypothetical protein from *Vibrio cholerae* V51, ZP_04918286.1; Lane 6—same material as Lane 5 but uninduced cells (negative control). FIG. 1B: Comparison of cultivation at 25° C. (Lanes 2, 3, 5, 7) and at 37° C. (Lanes 4, 8). Lane 1—Mark12 molecular weight marker (Invitrogen); Lane 2—hypothetical protein VIBHAR_03113, *Vibrio harveyi* ATCC BAA-1116, YP_001446289, uninduced cells (negative control); Lanes 3 and 4—hypothetical protein VIBHAR_03113, *Vibrio harveyi* ATCC BAA-1116, YP_001446289; Lanes 5 and 6—hypothetical protein lpg0647 [*Legionella pneumophila* subsp. *pneumophila* str. Philadelphia 1], YP_094683.1; Lanes 7 and 8—IS4 family transposase TnpA [*Legionella pneumophila* subsp. *pneumophila* str. Philadelphia 1], YP_094196.1.

FIG. 2 is a picture of an agarose gel electrophoresis run of lambda DNA digested with a naturally occurring transposase in the presence of magnesium ions or manganese ions for 30 minutes FIG. 2A or 2.5 hours FIG. 2B. The data show a significant improvement in the activity of the transposase and reduced specificity in the presence of manganese ions. Purified Vibhar transposase with a protein concentration of 3 mg/ml in 20 mM PIPES pH 7.5, 0.25 M KCl, 50% glycerol was mixed with the equal volume of adapter 78 at 50 uM concentration and incubated at room temperature for 1 hour, resulting in formation of the adapter/transposase complex, or "loaded transposase". 1.2 ul of the loaded transposase was transferred into 19 ul of the reaction mixture containing λ DNA at 10 ug/ml concentration, adapter 78 at 3 uM concentration, 10 mM MnCl2 or 10 mM $MgCl_2$, 25 mM Tris-acetate pH 7.5, 75 mM potassium glutamate. Reaction mixtures were incubated at 37° C. for 30 min or 2.5 hours, amplified in PCR using primer 7, separated in 1.8% agarose, and stained with ethidium bromide.

DETAILED DESCRIPTION OF VARIOUS EMBODIMENTS OF THE INVENTION

Figure 3:
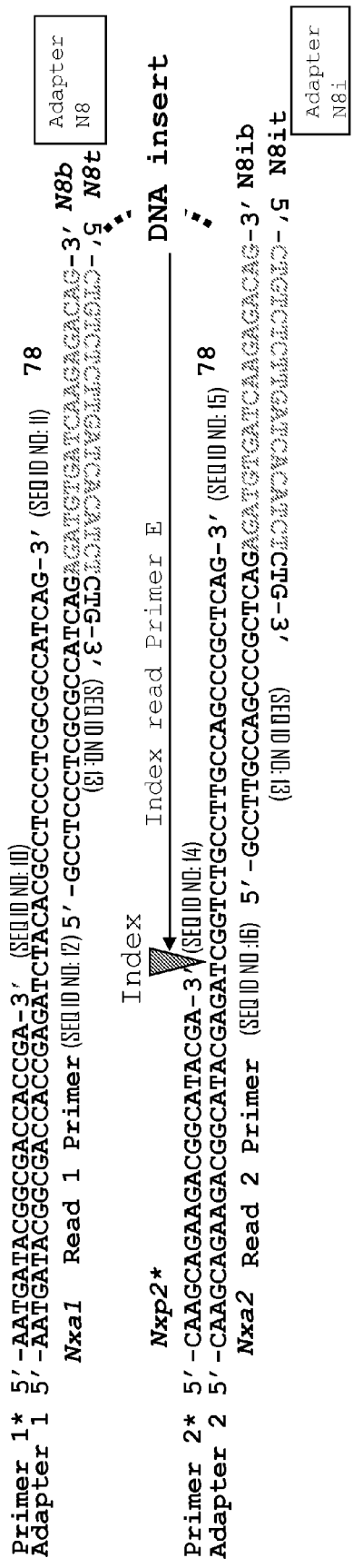
FIG. 3A and FIG. 3b show a comparison of the NEXTERA™ technology of Epicentre and the presently disclosed technology, showing the simplicity of the present technology as compared to the technology available in the art.
Figure 3:
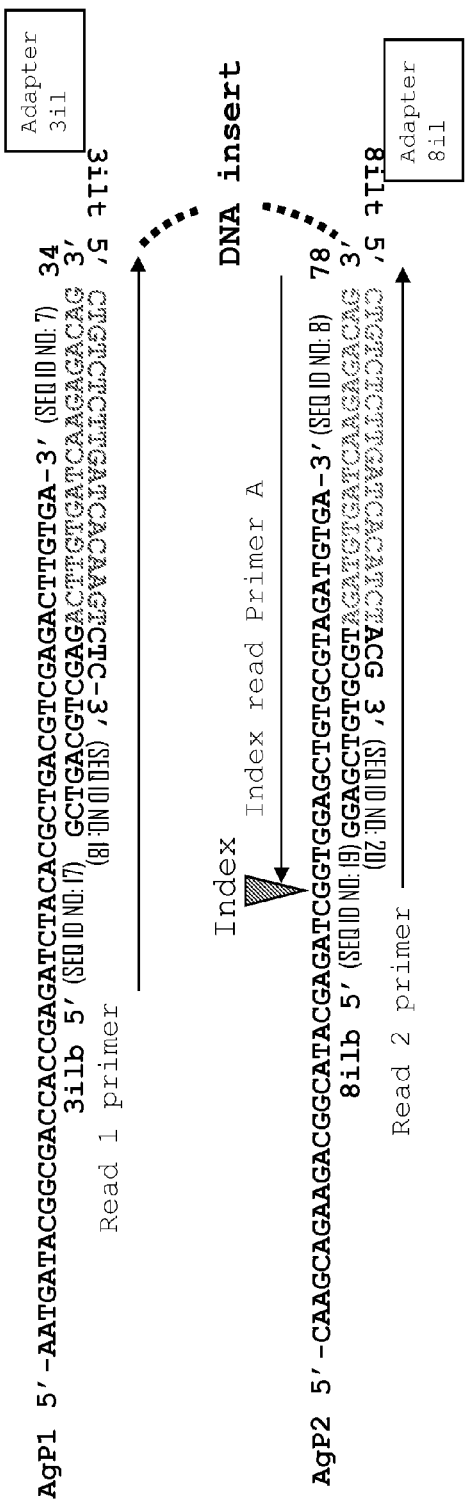

Reference will now be made in detail to various exemplary embodiments of the invention, data supporting such embodiments being illustrated in the accompanying drawings. This detailed description is not to be considered a limitation of the invention, but should rather be understood as a disclosure that provides the reader a more detailed description of certain aspects, features, and embodiments of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a transposase" includes a plurality of such transposases and reference to "the sample" includes reference to one or more samples and equivalents thereof known to those skilled in the art, and so forth. Furthermore, the use of terms that can be described using equivalent terms include the use of those equivalent terms.

Improved Transposase Reaction Conditions

Native transposases are believed to be inherently inactive. However, it is to be recognized that not all possible reaction conditions have been exhaustively tried. Here, it is disclosed that dramatic improvements in native DNA fragmentation activity of unmodified transposases can be achieved by introducing one or more transition-metal ion, including both Mg(II) and Mn(II), but preferably at least Mn(II), into the transposase reaction mixture. By the same approach, dramatic reduction in DNA fragmentation specificity was also achieved. It has to be stressed that low specificity is preferred for next generation sequencing for eliminating bias and achieving the best possible DNA library sequence coverage.

By the way of example, *Vibrio harveyi* transposase was identified and used in these experiments. Native and modified DNA recognition sequences for the enzyme were used, and are disclosed. Also disclosed are oligonucleotide designs that are useful in combination with the transposase for fragmenting DNA and for providing specific tags for next generation sequencing as well as indexes useful when a mixture of DNA libraries is sequenced on the same chip.

As discussed above, Tn5 transposase is problematic for various reasons. As such, the inventor evaluated various transposases from different genomes that are available on the NCBI web site. Some of them were annotated as transposases by the NCBI, but others were missed by their bioinformatics specialists, provisionally marked as "hypothetical protein". By analyzing proteins having sequence identity to known transposases, a collection of entries that appeared to be transposases that function by a "cut and paste" mechanism, which is useful for DNA fragmentation and tagging, were identified. Out of these, proteins were prioritized based on number of copies per genome and distribution among organisms (traits that are unlike Tn5, which is limited in copy number and host). The rationale was that such "ubiquitous" transposases are likely to be more active. The naturally occurring *Vibrio harveyi* transposase was used in most experiments and is herein referred to as "Vibhar". The Vibhar transposase gene is present in at least 21 copies in the *Vibrio harveyi* genome, and highly similar genes are widespread in other *Vibrio* genomes, whereas Tn5 transposase gene is present in one copy per genome and only in very few bacteria strains.

Using bioinformatics means, the IRL sequence for the transposase was identified as 5'-ctgtctcttatacacaat-3' (SEQ ID NO:9) and the IRR sequence as 5'-acttgtgatcaagagacag-3' (SEQ ID NO:4). Through experimentation, a modified 19 bp IRR sequence 5'-agatgtgatcaagagacag-3' (SEQ ID NO:5) proved to be more efficient and was used in most experiments. A double stranded oligonucleotide of this sequence hereinafter is referred to as adapter 78. Apart from being "ubiquitous", other reasons for focusing on Vibhar transposase was that it is very easy to produce due to its very high expression level in *E. coli* as a soluble protein, with the expression level by far superior to Tn5 and to most of the evaluated transposases (see FIG. 1, which shows a comparison of expression levels for various transposases tested). Furthermore, unlike with Tn5 transposase, practically no proteolytic degradation of Vibhar transposase was observed. When initially tested, purified Vibhar transposase had only weak activity in conditions traditionally used for DNA fragmentation. Furthermore, the yield of DNA fragments of about 200-800 bp, which are most useful in next generation DNA sequencing, was unsatisfactory. Most of the generated fragments were of a much larger size. Moreover, prominent DNA fragment bands were observed, indicating considerable sequence specificity, which is undesirable in samples for DNA sequencing. The above problems were not alleviated at increased incubation times with the transposase.

However, these problems were resolved by substituting Mn(II) ion for Mg(II), or by supplementing Mg(II) with Mn(II), noting that Mg(II) is routinely used in transposase reactions. (FIG. 2). In addition, it was found that the previously noted problems relating to Mg(II) ions could be overcome by the present methods. Further improvement was achieved by lowering the potassium glutamate concentration to 25 mM from 75-100 mM, which is routinely used for reactions with Tn5 transposase and by raising the reaction temperature to 47° C.

By the way of example, the following conditions can be used to achieve satisfactory DNA fragmentation: Purified transposase with the protein concentration 3 mg/ml in 20 mM PIPES pH 7.5, 0.25 M KCl, 50% glycerol is mixed with an equal volume of adapter 78 at 50 uM concentration and incubated at room temperature for 1 h, resulting in formation of the adapter/transposase complex, or "loaded transposase". 1.2 ul of the loaded transposase is transferred into 19 ul of the reaction mixture containing lambda DNA at 10 ug/ml concentration, adapter 78 at 3 uM concentration, 10 mM $MnCl_2$, 25 mM Tris-acetate pH 7.5, 25 mM potassium glutamate. An equivalent concentration of $MgCl_2$ could be substituted, or added (either to achieve an additive molar concentration or a collective molar concentration) for/to the $MnCl_2$. Incubate the reaction mixture at 47° C. for 20 min. Remove oligonucleotides using StrataPrep® PCR purification kit (Agilent, La Jolla, Calif.). Amplify DNA fragments using PCR using a primer having the sequence 5'-agatgtgatcaagagacag-3' (SEQ ID NO:5) at 4 uM concentration, Pfu Ultra® HF (Agilent Technologies, La Jolla, Calif.) at a concentration of 83 units/ml, dNTPs at 1 mM concentration, on 1×PfuUltra® buffer. Apply one cycle at 72° C. for 4 min, followed by 20 cycles: 94° C. 40 sec, 56° C. 45 sec, 72° C. 2 min, followed by one cycle at 72° C. for 10 min.

This design allows satisfactory DNA fragmentation, but it does not provide for attachment of different polynucleotide sequences to each end of the DNA fragments. However, next generation DNA sequencing requires providing every DNA fragment with a different DNA sequence at each end (i.e., providing tags).

Originally Illumina (San Diego, Calif.) developed technology for DNA fragmentation and tagging DNA fragments for next generation DNA sequencing (Nature Methods, 5, p 887-893, 2008). However, the Illumina method for DNA fragmentation and tagging is rather complex and laborious. Therefore, a much more simple method for DNA fragmentation and tagging was developed by Epicentre Biotechnologies, Madison, Wis., using a Tn5 transposase. However, this resulted in some compromises in oligonucleotide design because a Tn5 transposase recognition sequence had to be added. As a result, oligonucleotides which are attached to the DNA fragments became considerably longer than in the Illumina design. Therefore, a more complex scheme for PCR amplification had to be employed, i.e., instead of two PCR primers as in the Illumina design, four PCR primers are used in the Epicentre design, and with a possibility of mis-priming on human DNA.

The oligonucleotide design represented in FIG. 3A is very similar to the design used by Epicentre (and may be designated herein as E). The difference from the Epicentre design is that the transposase recognition sequence is different. The Epicentre design uses a 19 bp "mosaic" Tn5 transposase recognition sequence, whereas the present invention uses a modified 19 bp *Vibrio harveyi* transposase recognition sequence (designated "78") due to the fact that the Vibhar transposase is used in the experiments disclosed herein. The drawback of the prior art design is utilization of 4 primers in PCR, designated in the figure as Primer 1* (SEQ ID NO:10) (alias Nxp1*), Primer 2* (SEQ ID NO:14) (alias Nxp2*), Adapter 1 (SEQ ID NO:11) (alias Nxa1), and Adapter 2 (SEQ ID NO:15) (alias Nxa2). At several initial PCR cycles, only Adapter 1 and Adapter 2 are used because Primer 1* and Primer 2* have no landing sites on the oligonucleotides containing transposase recognition sequences during these cycles. These initial cycles are less efficient, as concentrations of Adapter 1 and Adapter 2 are about 20 times less than the concentrations that are typically recommended in PCR reactions. Later on, Primer 1* and Primer 2* have landing sites and participate in the PCR reaction. These are present at optimal concentrations for PCR amplification and by the end of the cycles, the overwhelming majority of PCR products are generated using these shorter primers.

However, a simple analysis of these shorter primers using the Primer 3 program showed that they are sub-optimal, with high 3' end stability and a high possibility of mis-priming on human DNA (FIG. 3A). Fragments generated as a result of such mis-priming would miss a landing site for a Read primer (FIG. 3A). For instance, if mis-priming was generated by Primer 2*, no sequencing information would be obtained from Read 2 Primer (SEQ ID NO:16) and from Index read Primer E, but "mis-primed" fragments would occupy valuable space on Illumina chips as Primer 2* provides all the necessary DNA sequence for the attachment to the chips. Unfortunately, a better Primer 1* and a better Primer 2* cannot be designed because their landing sites are within the Illumina tag sequences. This leaves practically no room for maneuver unless the Illumina chips are re-designed. It is important to stress that the original Illumina design does not have such problems.

Improved System for DNA Fragmenting and Tagging by Transposases

This portion of the disclosure supplements the previous portion of the disclosure and provides oligonucleotide design to achieve improved yield of DNA fragments as compared to the prior art design. Unlike in the prior art design, the 3' end of the primers for PCR amplification according to this aspect of the invention is located within the transposase recognition sequence. This is facilitated by the use of two different oligonucleotide transposase recognition sequences, which are used to attach two different Illumina tags, contrary to the prior art design where just one transposase sequence is used to attach different tags. Furthermore, it is to be understood that, in embodiments, the invention encompasses conditions for tagging, in accordance with the conditions discussed above with respect to conditions for transposase reaction conditions. In some applications, such conditions are preferred and, in embodiments, provide improved conditions as compared to prior art disclosures of such conditions.

As a result, more efficient 2-primer amplification was achieved as compared to the less efficient 4-primer amplification used in the prior art design. The 2-primer scheme of the present invention results in a better yield of DNA fragments as compared to the prior art design of the Nextera kit (Epicentre), and the possibility of mis-priming on human DNA library was reduced compared to the prior art design.

The main difference between the present design and the Epicentre design is that the former design uses 2 different transposase recognition sequences, referred to herein in an exemplary embodiment as "78" and "34", each attached to a different Illumina tag, whereas in the latter design, only one transposase recognition sequence is used for both tags (see FIG. 3). The present design allows for shifting the PCR primers 3' into the transposase recognition DNA sequence and allows use of overall shorter oligonucleotides and more efficient 2-primer PCR amplification with practically no possibility of mis-priming on human DNA.

To overcome the problems of the prior art while simplifying the design, the inventor came up with a design which allowed bringing the combined size of the nucleotides attached to the DNA fragments down to about the same size as in the "Paired End" design of Illumina. The design also avoids using 4-primer PCR with short primers having landing sites within the Illumina tags. By using 2 Vibhar transposase recognition sequences ("78" and "34") and re-designing the area in between Illumina tags and transposase recognition sequences, the possibility of mis-priming on human DNA was minimized. Either design allows insertion of about 1-8 nucleotide "indexes", designated by the triangles in FIG. 3. Such indexes are useful to identify sequence reads coming from specific DNA libraries when several libraries are sequenced on the same chip.

To achieve DNA fragmentation and tagging, oligonucleotide 3ilb (SEQ ID NO:17) was hybridized with oligonucleotide 3ilt (SEQ ID NO:18), and oligonucleotide 8ilb (SEQ ID NO:19) was hybridized with oligonucleotide 8 ilt (SEQ ID NO:20). An equimolar mixture of the hybridized oligonucleotides was used to load Vibhar transposase and fragment phage lambda DNA exactly as described above except the oligonucleotides were different. After the spin-column purification from un-incorporated oligonucleotides, fragmented and tagged DNA was amplified using AgP1 (SEQ ID NO:7) and AgP2 (SEQ ID NO:8) primers (at 2 uM each) for 20 cycles. PicoMaxx® DNA polymerase was used for amplification according to the manufacturer's instruction (Agilent, La Jolla, Calif.).

For comparison with the Epicentre design, oligonucleotide N8t (SEQ ID NO:13) was hybridized either with oligonucleotide Read 1 Primer (SEQ ID NO:12) or with Read 2 primer (SEQ ID NO:16) (FIG. 3B). An equimolar mixture of the hybridized oligonucleotides was used to load Vibhar transposase and fragment phage lambda DNA exactly as described above. After the spin-column purification from un-incorporated oligonucleotides, fragmented and tagged DNA was amplified for 20 cycles using a mixture of Primer 1*, Primer 2* (at 2 uM concentration each), Adapter 1, Adapter 2 (at 0.1 uM concentration each). PicoMaxx® or PfuUltra® thermo-stable polymerase was used for amplification according to the manufacturer's instructions (Agilent, La Jolla, Calif.).

Figure 4:
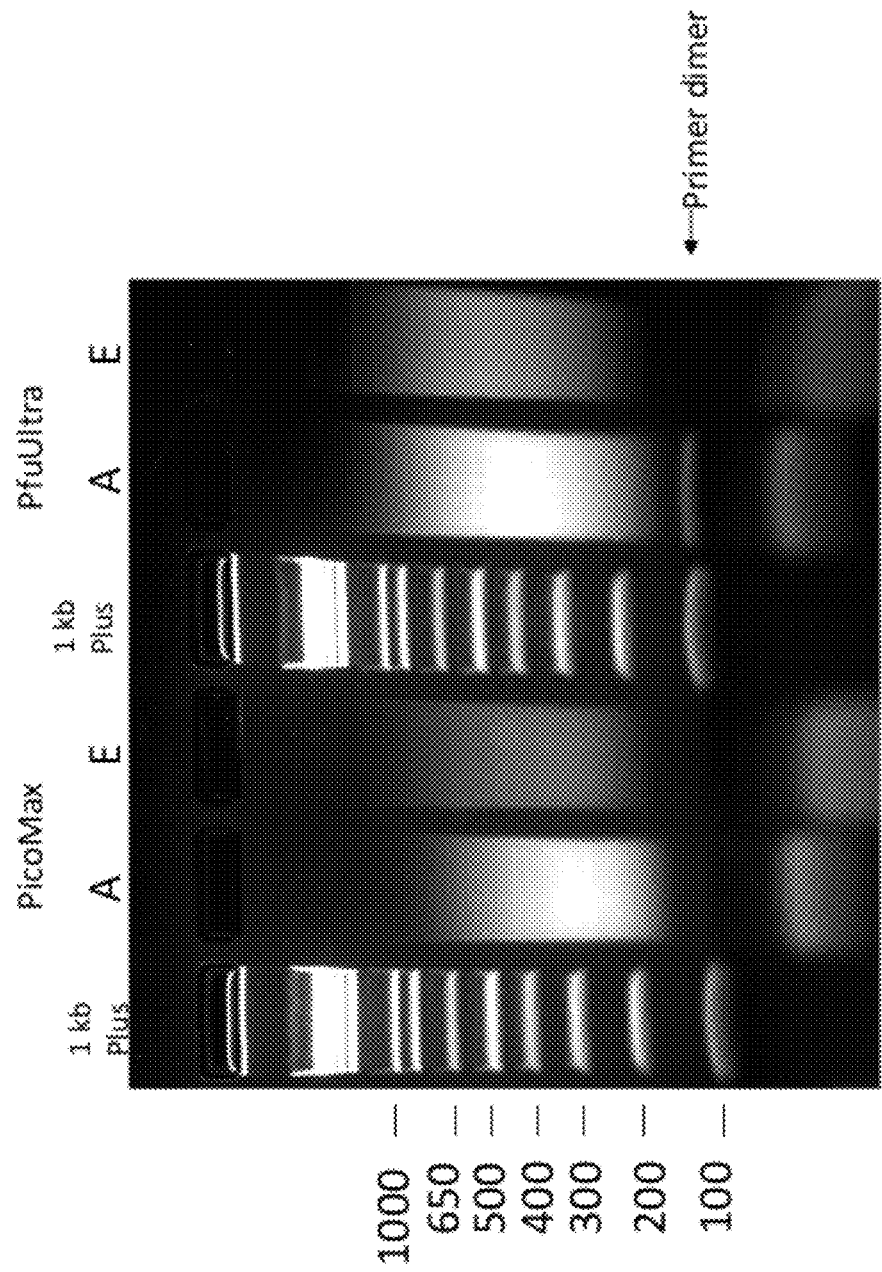
FIG. 4 shows an agarose gel electrophoresis run of fragmenting and tagging of lambda DNA using an exemplary naturally occurring transposase and either one or two different recognition sequences for that transposase, showing that cleavage, tagging, and efficiency of amplification is superior with the design utilizing two recognition sequences. DNA fragmentation, PCR amplification using PicoMaxx® and PfuUltra® polymerase, and analysis of the generated fragments was performed as described in the Detailed Protocol for DNA Fragmentation and Tagging Using Vibhar. After PCR, fragments were not purified from oligonucleotides. 1 kb Plus DNA ladder was from Invitrogen Inc., Carlsbad, Calif., and was used for comparison.
Figure 5:
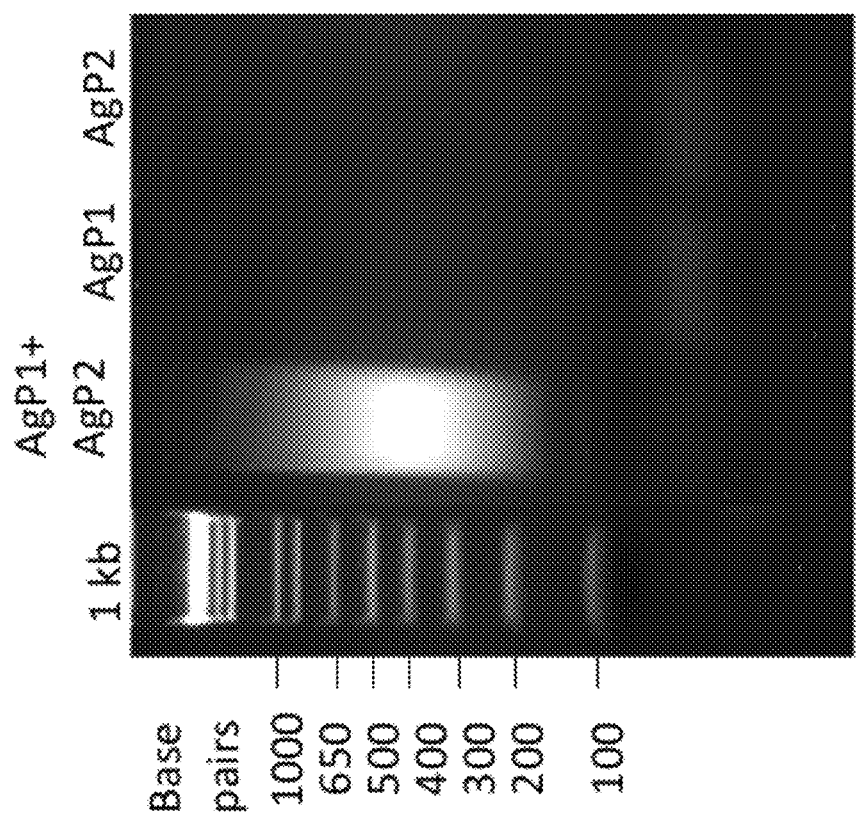
FIG. 5 shows an agarose gel electrophoresis run of fragmenting and tagging of lambda DNA using an exemplary naturally occurring transposase and two different recognition sequences for that transposase, showing that amplification only occurs when both recognition sequences are incorporated into the target DNA. DNA fragmentation, PCR amplification using PicoMaxx® polymerase, and analysis of the generated fragments was performed as described in the Detailed Protocol for DNA Fragmentation and Tagging Using Vibhar. After PCR, fragments were not purified from oligonucleotides. 1 kb Plus DNA ladder (Invitrogen Inc., Carlsbad, Calif.) was used for comparison.
Figure 6:
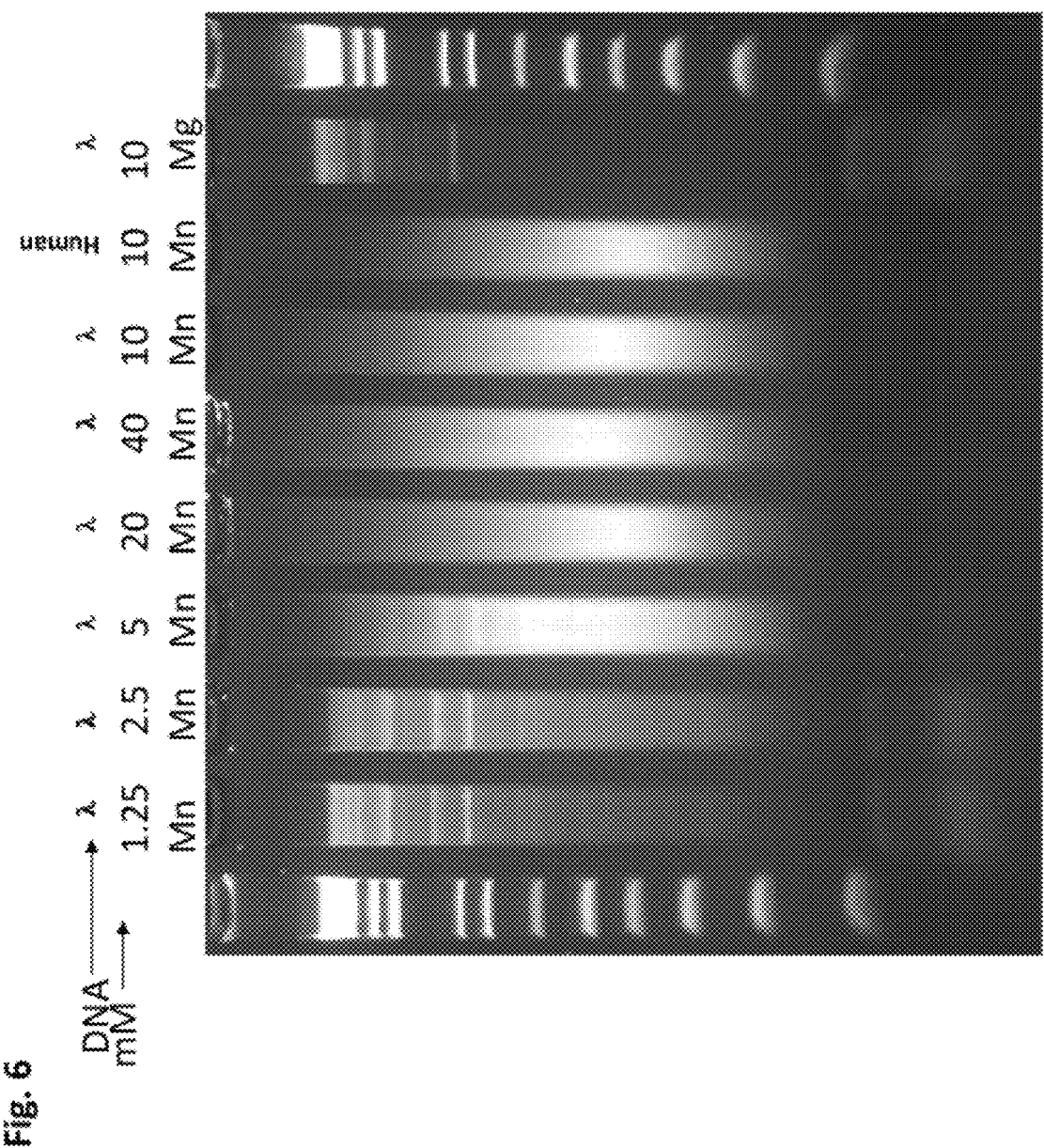
FIG. 6 shows additional results comparing the activity of a naturally occurring transposase in varying concentrations of Mn(II) and a comparison to Mg(II), as well as showing that fragmentation, tagging, and PCR amplification observed on target lambda DNA and human DNA are comparable. DNA fragmentation, PCR amplification using PfuUltra® polymerase, and analysis of the generated fragments was performed as described in the Detailed Protocol for DNA Fragmentation and Tagging Using Vibhar except different concentrations of Mn++ or Mg++ instead of Mn++ were used. After PCR, fragments were not purified from oligonucleotides. 1 kb Plus DNA ladder (Invitrogen Inc., Carlsbad, Calif.) was used for comparison.

Amplified DNA fragments were separated in 2% agarose-TBE gels and stained with ethidium bromide (FIG. 4). As follows from the data represented in the figure, amplification using the present design clearly provides a better yield of DNA fragments. The fragments are of the size range useful in next generation DNA sequencing. DNA was amplified exclusively when both PCR primers were present, indicating that each fragment was tagged with different Illumina tags at the ends (FIG. 5). Similar results were obtained with lambda DNA and with human DNA, indicating that present design is applicable to diverse genomes, and it was also confirmed that with the present design, which is suitable for next generation DNA sequencing, DNA fragmentation using $Mn^{+2}$ ions is more efficient than with $Mg^{+2}$ at a typical concentration (FIG. 6).

In addition to oligonucleotide designs represented in FIG. 3, other designs can be also used. For example, both Illumina tags could be incorporated into the same adapter, resulting in "branched" adapter. This applies to Roche or other tags which can be designed by those skilled in the art. Whole or part of the Ilumina, Roche, or other tags could be added in PCR reaction to adapter 78 or extended adapter 78 or a similar adapter, rather than being completely incorporated from the very start into the adapter, this is being applicable to a mix of 2 adapters as depicted in FIG. 3, as wells as to branched adapters. Furthermore, 2 adapters can be connected with a spacer to ensure loading each transposase dimer with different adapters, i.e., 2 adapters, 1 different adapter copy per transposase dimer.

Detailed Protocol for DNA Fragmenting and Tagging Using Vibhar

A. Hybridizing Oligonucleotides to Produce Partially ds Adapters for Loading Vibhar Transposase Dissolve the oligonucleotides depicted on FIG. 3 to 100 uM concentration in deionized sterile water (for each nm oligo add 10 ul of water).

1. Mix equal volumes of N8t (SEQ ID NO:13) with N8b (SEQ ID NO:12), N8it (SEQ ID NO:13) with N8ib (SEQ ID NO:16), 3ilt (SEQ ID NO:18) with 3ilb (SEQ ID NO:17), 8ilt (SEQ ID NO:20) with 8ilb (SEQ ID NO:19).
2. To each mix add 1/19 volume of 0.2 M Tris-Acetate pH 7.5, 0.5 M potassium glutamate.
3. Heat about 400 ml of water to 72° C. in 500 ml beaker, place the mixtures into a floatie in the beaker, wrap in a plastic bag and cool slowly on the bench to room temperature over several hours.
4. The resulting adapters are designated N8 (derived from oligonucleotides N8t and N8b), N8i (from N8it and N8ib), 3il (from 3ilt and 3ilb), 8il (from 8ilt and 8ilt). See FIG. 3.
5. Store the adapters at −20° C.

B. Preparing Vibhar Buffer (25 mM Tris-Acetate pH7.5, 25 mM Potassium Glutamate 10 mM MnCl2 when 1×).

Mix the following to prepare 1 ml of 4× buffer:
1. 200 ul of 0.5 M Tris-acetate pH 7.5
2. 100 ul of 1M Potassium glutamate
3. 80 ul of 0.5 M $MnCl_2$
4. 620 ul of deionized water.

C. Loading Vibhar Transposase with Adapters
1. Mix 10 ul of adapter N8 with 10 ul adapter N8I. Mix 10 ul of adapter 3il with 10 ul of adapter 8il.
2. Mix 4 ul of Vibhar transposase (3 mg/ml in 20 mM PIPES pH 7.5, 0.25 M KCl, 50% glycerol) with 4 ul of N8/N8i mix or with 4 ul of 3il/8il adapter mix.
3. Incubate at room temperature for 70-80 min.

D. DNA Fragmentation

Mix:
1. 20 ul of 4× Vibhar buffer
2. 20 ul lambda DNA @ 40 ug/ml
3. 10 ul of N8/N8i mix or 3il/8il mix
4. 30 ul water Add 70 ul of the mix to 8 ul of the loaded transposase. Incubate at 47° C. for 20-25 min.

E. Spin-Column Purification

To each sample of fragmented DNA add equal volume (78 ul) of binding buffer (4M guanidinium hydrochloride), vortex and apply the mix onto Single GFF layer Retainer Ring Versa Spin column (part of Absolutely RNA Nanoprep Kit, Agilent). Place the column into 2 ml cap-less receptacle tube.

1. Spin at 14,800 RPM for 34 sec in the inner ring of Beckman-Coulter Microfuge® 16.
2. Completely remove flow-through from the receptacle tube, re-insert the column, apply 200 ul of the washing buffer (80% Absolute Ethanol, 200 proof, Molecular biology grade, Fischer Scientific).
3. Spin as before.
4. Repeat steps 2 and 3.

5. Completely remove flow-through from the receptacle tube, re-insert the column and spin as before.
6. Transfer the column into a cap-less 1.5 ml Eppendorf tube, apply 30 ul of 10 mM Tris-HCl buffer pH 8.46 to the top of the column and incubate at room temperature for 5 min.
7. Spin as before.
8. Apply 30 ul of water and spin as before.
9. Transfer united eluates into a tube with a cap.

F. PCR Amplification

Primer Mixes:

Dissolve all primers (FIG. 3) in water to 100 uM concentration.

Primer Mix A (for Agilent design). Mix 100 ul of AgP1 (SEQ ID NO:7) with 100 ul of AgP2 (SEQ ID NO:8).

Primer Mix E (for Epicentre design). Mix 100 ul of Nxp1*, 100 ul of Nxp2*, 5 ul Nxa1 and 65 ul Nxa2.

TABLE 1

Reaction Mixes

| For eight 20 ul reaction (with excess) mix: | For two 20 ul reactions: |
|---|---|
| 20 ul 10x PicoMaxx(R) buffer* | 5 ul 10x PicoMaxx(R) buffer |
| 2 ul 100 mM dNTPs | 5 ul 10 mM dNTPs |
| 8 ul of primers mix A or primers mix E | 2 ul primers mix A or primers mix E |
| 6.7 ul PicoMaxx(R) polymerase* | 1.7 ul PicoMaxx(R) polymerase |
| 113.3 ul water | 23.8 ul water |

*PfuUltra with its buffer can be used as well. The yield is about the same, but there is more primer-dimer with PfuUltra (FIG. 4).

Aliquot 5 ul of fragmented DNA from step E into the wells of a PCR plate. Add 15 ul of the above mix into the wells.

| Amplify on Agilent SureCycler 8800 using following parameters: | | |
|---|---|---|
| Repair | 72° C. | 2 min 22 sec |
| Denaturation | 95° C. | 3 min |
| 19 cycles of: | | |
| Denatuaration | 93° C. | 40 sec |
| Annealing | 59° C. | 1 min |
| Elongation | 72° C. | 3 min |
| End cycle: | | |
| Elongation | 72° C. | 10 min |
| Refrigerate | 4° C. | infinite |

Analyze using 2% agarose TBE gel. For cloning into plasmid vectors or for sequencing on Illumina chips, purify from un-reacted oligos using StrataPrep® PCR Purification kit (Agilent, La Jolla, Calif.) according to the manufacturer's instructions.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only.

The invention claimed is:

1. An in vitro method for DNA fragmentation of a target DNA molecule, said method comprising:
   combining:
   a) a first DNA adapter comprising at least a portion that is double stranded, wherein the double stranded portion comprises a first recognition sequence for a transposase and the first DNA adapter further comprises a first non-recognition sequence for the transposase;
   b) a second DNA adapter comprising at least a portion that is double stranded, wherein the double stranded portion comprises a second recognition sequence for the transposase and the second DNA adapter further comprises a second non-recognition sequence for the transposase, wherein the second non-recognition sequence is different from the first non-recognition sequence; and
   c) the transposase,
   wherein combining a), b), and c) forms a loaded transposase; and
   combining the loaded transposase with a target DNA molecule and $Mg^{+2}$ ions, $Mn^{+2}$ ions, or both $Mg^{+2}$ ions and $Mn^{+2}$ ions under conditions whereby the loaded transposase associates with the target DNA and cleaves the target DNA molecule via transposase-mediated cleavage to provide a cleaved DNA product,
   wherein the first recognition sequence and the second recognition sequence are different.

2. The method of claim 1, wherein the transposase is an IS4 family transposase.

3. The method of claim 2, wherein the transposase is naturally found in *Vibrio* species.

4. The method of claim 3, wherein the transposase is a transposase from *Vibrio harveyi*.

5. The method of claim 1, wherein the first recognition sequence, the second recognition sequence, or both, are recognition sequences for a transposase from *Vibrio harveyi*.

6. The method of claim 5, wherein the first recognition sequence, the second recognition sequence, or both, are modified recognition sequences for a transposase from *Vibrio harveyi* that differ from the naturally occurring recognition sequences by at least one nucleotide.

7. The method of claim 1, wherein the $Mn^{+2}$ ion concentration, the $Mg^{+2}$ ion concentration, or the combined $Mn^{+2}$ ion concentration and $Mg^{+2}$ ion concentration is between about 1 mM and about 100 mM.

8. The method of claim 1, wherein the $Mn^{+2}$ ion concentration, the $Mg^{+2}$ ion concentration, or the combined $Mn^{+2}$ ion concentration and $Mg^{+2}$ ion concentration is between about 5 mM and about 40 mM.

9. The method of claim 1, wherein the first non-recognition sequence, the second non-recognition sequence, or both comprise a tag sequence for binding of amplified product from the cleaved DNA product to a solid support.

10. A method for in vitro combined DNA fragmentation and tagging of a target DNA molecule, said method comprising:
  combining:
    a) the target DNA molecule;
    b) a first DNA adapter comprising at least a portion that is double stranded, wherein the double stranded portion comprises a first recognition sequence for a transposase;
    c) a second DNA adapter comprising at least a portion that is double stranded, wherein the double stranded portion comprises a second recognition sequence for the transposase; and
    d) the transposase,
  subjecting the combination of a), b), c), and d) to association and cleavage conditions whereby the first DNA adapter, second DNA adapter, and transposase can form a loaded transposase, associate with the target DNA molecule, and cleave the target DNA molecule via transposase-mediated cleavage to provide a cleaved and tagged DNA product, wherein the association and cleavage conditions include 1-100 mM $Mn^{+2}$, $Mg^{+2}$, or both each at that concentration range, wherein the first recognition sequence is different from the second recognition sequence.

11. The method of claim 10, wherein the first DNA adapter, the second DNA adapter, and the transposase are combined to make a complex prior to combining the complex with the target DNA molecule.

12. The method of claim 10, wherein the transposase is an IS4 family transposase.

13. The method of claim 10, wherein the transposase is naturally found in *Vibrio* species.

14. The method of claim 13, wherein the transposase is a transposase from *Vibrio harveyi*.

15. The method of claim 10, wherein the transposase is a mutant form of a naturally occurring transposase.

16. The method of claim 10, wherein potassium ions are present in the cleavage conditions at a concentration of less than 50 mM.

17. The method of claim 10, wherein the $Mn^{+2}$ concentration, the $Mg^{+2}$ concentration, or the combined $Mn^{+2}$ concentration and $Mg^{+2}$ concentration in the cleavage conditions is between about 5 mM and about 40 mM.

18. The method of claim 10, wherein the $Mn^{+2}$ concentration, the $Mg^{+2}$ concentration, or the combined $Mn^{+2}$ concentration and $Mg^{+2}$ concentration in the cleavage conditions is between about 10 mM and about 20 mM.

19. The method of claim 1, wherein the second combining step is carried out by combining the loaded transposase with said target DNA molecule and $Mn^{+2}$ ions.

20. The method of claim 10, wherein said association and cleavage conditions include 1-100 mM $Mn^{+2}$.

21. An in vitro method for DNA fragmentation of a target DNA molecule, said method comprising:
  combining:
    a) a first DNA adapter comprising at least a portion that is double stranded, wherein the double stranded portion comprises a first recognition sequence for a transposase and the first DNA adapter further comprises a first non-recognition sequence for the transposase;
    b) a second DNA adapter comprising at least a portion that is double stranded, wherein the double stranded portion comprises a second recognition sequence for the transposase and the second DNA adapter further comprises a second non-recognition sequence for the transposase, wherein the first non-recognition sequence is different from the second non-recognition sequence of the first DNA adapter; and
    c) the transposase,
  wherein combining the a), b), and c) forms a loaded transposase; and
  combining the loaded transposase with a target DNA molecule and $Mn^{+2}$ ions under conditions whereby the loaded transposase associates with the target DNA and cleaves the target DNA molecule via transposase-mediated cleavage to provide a cleaved DNA product.

22. A method for in vitro combined DNA fragmentation and tagging of a target DNA molecule, said method comprising:
  combining:
    a) the target DNA molecule;
    b) a first DNA adapter comprising at least a portion that is double stranded, wherein the double stranded portion comprises a first recognition sequence for a transposase;
    c) a second DNA adapter comprising at least a portion that is double stranded, wherein the double stranded portion comprises a second recognition sequence for the transposase; and
    d) the transposase,
  subjecting the combination of a), b), c), and d) to association and cleavage conditions whereby the first DNA adapter, second DNA adapter, and transposase form a loaded transposase, associate with the target DNA molecule, and cleave the target DNA molecule via transposase-mediated cleavage to provide a cleaved and tagged DNA product, wherein the association and cleavage conditions include 1-100 mM $Mn^{+2}$.

* * * * *

UNITED STATES PATENT AND TRADEMARK OFFICE
CERTIFICATE OF CORRECTION

PATENT NO.         : 9,005,935 B2
APPLICATION NO.    : 13/470087
DATED              : April 14, 2015
INVENTOR(S)        : Belyaev Page 1 of 1

It is certified that error appears in the above-identified patent and that said Letters Patent is hereby corrected as shown below:

On the Title Page

Item (56), in column 2, under "Other Publications", line 28, delete "Vo.1" and insert -- Vol. --, therefor.

Item (56), in column 2, under "Other Publications", line 42, delete "Structual" and insert -- Structural --, therefor.

In the Specification

Column 2, line 33, delete "Bioi." and insert -- Biol. --, therefor.

Column 2, line 38, delete "Bioi." and insert -- Biol. --, therefor.

Column 15, line 24, delete "8 ilt" and insert -- 8ilt --, therefor.

Column 18, line 11, delete "Denatuaration" and insert -- Denaturation --, therefor.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 20

<210> SEQ ID NO 1
<211> LENGTH: 4
<212> TYPE: PRT
<213> ORGANISM: Vibrio harveyi

<400> SEQUENCE: 1

Tyr Arg Glu Lys
1

<210> SEQ ID NO 2
<211> LENGTH: 5
<212> TYPE: PRT
<213> ORGANISM: Vibrio harveyi

<400> SEQUENCE: 2

Asp Arg Glu Ala Asp
1               5

<210> SEQ ID NO 3
<211> LENGTH: 19
<212> TYPE: DNA
<213> ORGANISM: Artificial sequence
<220> FEATURE:
<223> OTHER INFORMATION: Recognition sequence for V. harveyi
      transposase.

<400> SEQUENCE: 3
ctgtctcttg atcacaagt                                                  19

<210> SEQ ID NO 4
```

```
<211> LENGTH: 19
<212> TYPE: DNA
<213> ORGANISM: Artificial Sequence
<220> FEATURE:
<223> OTHER INFORMATION: Recognition sequence for V. harveyi
      transposase.

<400> SEQUENCE: 4
acttgtgatc aagagacag                                                 19

<210> SEQ ID NO 5
<211> LENGTH: 19
<212> TYPE: DNA
<213> ORGANISM: Artificial Sequence
<220> FEATURE:
<223> OTHER INFORMATION: Recognition sequence for V. harveyi
      transposase.

<400> SEQUENCE: 5
agatgtgatc aagagacag                                                 19

<210> SEQ ID NO 6
<211> LENGTH: 19
<212> TYPE: DNA
<213> ORGANISM: Artificial Sequence
<220> FEATURE:
<223> OTHER INFORMATION: Recognition sequence for V. harveyi
      transposase.

<400> SEQUENCE: 6
ctgtctcttg atcacatct                                                 19

<210> SEQ ID NO 7
<211> LENGTH: 49
<212> TYPE: DNA
<213> ORGANISM: Artificial Sequence
<220> FEATURE:
<223> OTHER INFORMATION: Primer

<400> SEQUENCE: 7
aatgatacgg cgaccaccga gatctacacg ctgacgtcga gacttgtga                49

<210> SEQ ID NO 8
<211> LENGTH: 48
<212> TYPE: DNA
<213> ORGANISM: Artificial Sequence
<220> FEATURE:
<223> OTHER INFORMATION: Primer

<400> SEQUENCE: 8
caagcagaag acggcatacg agatcggtgg agctgtgcgt agatgtga                 48

<210> SEQ ID NO 9
<211> LENGTH: 18
<212> TYPE: DNA
<213> ORGANISM: Vibrio harveyi

<400> SEQUENCE: 9
ctgtctctta tacacaat                                                  18

<210> SEQ ID NO 10
<211> LENGTH: 20
<212> TYPE: DNA
<213> ORGANISM: Artificial Sequence
<220> FEATURE:
<223> OTHER INFORMATION: Primer
```

```
<400> SEQUENCE: 10
aatgatacgg cgaccaccga                                               20

<210> SEQ ID NO 11
<211> LENGTH: 48
<212> TYPE: DNA
<213> ORGANISM: Artificial Sequence
<220> FEATURE:
<223> OTHER INFORMATION: Adapter to allow amplification from primers

<400> SEQUENCE: 11
aatgatacgg cgaccaccga gatctacacg cctccctcgc gccatcag                48

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
gcctccctcg cgccatcaga gatgtgatca agagacag                          38

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ctgtctcttg atcacatctc tg                                            22

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
caagcagaag acggcatacg a                                             21

<210> SEQ ID NO 15
<211> LENGTH: 49
<212> TYPE: DNA
<213> ORGANISM: Artificial Sequence
<220> FEATURE:
<223> OTHER INFORMATION: Adapter to allow amplification of sequences

<400> SEQUENCE: 15
caagcagaag acggcatacg agatcggtct gccttgccag cccgctcag              49

<210> SEQ ID NO 16
<211> LENGTH: 38
<212> TYPE: DNA
<213> ORGANISM: Artificial Sequence
<220> FEATURE:
<223> OTHER INFORMATION: Oligonucleotide for linking other nucleic acid
      sequences

<400> SEQUENCE: 16
gccttgccag cccgctcaga gatgtgatca agagacag                          38

<210> SEQ ID NO 17
```

```
<211> LENGTH: 31
<212> TYPE: DNA
<213> ORGANISM: Artificial Sequence
<220> FEATURE:
<223> OTHER INFORMATION: Adaptor/linker to allow amplification of
      nucleic acids

<400> SEQUENCE: 17
gctgacgtcg agacttgtga tcaagagaca g                                31

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ctgtctcttg atcacaagtc tc                                          22

<210> SEQ ID NO 19
<211> LENGTH: 31
<212> TYPE: DNA
<213> ORGANISM: Artificial Sequence
<220> FEATURE:
<223> OTHER INFORMATION: Linker to allow amplification of nucleic acids

<400> SEQUENCE: 19
ggagctgtgc gtagatgtga tcaagagaca g                                31

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ctgtctcttg atcacatcta cg                                          22
```